United States Patent [19]
Jakobsen et al.

[11] Patent Number: 5,874,274
[45] Date of Patent: *Feb. 23, 1999

[54] PROCESSING PLANT MATERIAL WITH XYLANASE

[75] Inventors: Tina Sejersgård Jakobsen, Copenhagen; Hans Peter Heldt-Hansen, Virum; Lene Venke Kofod, Uggerløse; Christian Lorentz Bagger, Frederiksberg; Anette Müllertz, Charlottenlund, all of Denmark

[73] Assignee: Novo Nordisk A/S, Bagsvaerd, Denmark

[ * ] Notice: The term of this patent shall not extend beyond the expiration date of Pat. No. 5,693,518.

[21] Appl. No.: 700,546
[22] PCT Filed: Feb. 24, 1995
[86] PCT No.: PCT/DK95/00082
    § 371 Date: Sep. 23, 1996
    § 102(e) Date: Sep. 23, 1996
[87] PCT Pub. No.: WO95/23514
    PCT Pub. Date: Sep. 8, 1995

[30] Foreign Application Priority Data

May 2, 1994 [DK] Denmark .................................. 0247/94

[51] Int. Cl.$^6$ ................ C12N 9/24; D21C 1/00; C12P 19/14

[52] U.S. Cl. ................ 435/200; 435/72; 435/99; 435/277; 435/274; 435/209

[58] Field of Search .......................... 435/72, 99, 277, 435/274, 200, 209

[56] References Cited

U.S. PATENT DOCUMENTS

4,144,354 3/1979 Unno et al. .................................. 426/2

FOREIGN PATENT DOCUMENTS

WO 91/19782 12/1991 WIPO .
WO 92/01793 2/1992 WIPO .
WO 93/25693 12/1993 WIPO .

*Primary Examiner*—Francisco Prats
*Attorney, Agent, or Firm*—Steve T. Zelson, Esq.; Valeta Gregg, Esq.

[57] ABSTRACT

The present invention relates to a process for reducing the viscosity of a plant material, which process comprises treating the plant material with a xylanase having i) a WSPS per mg protein added which is higher than 0,06, and/or ii) a WSPU per mg protein added which is higher than 15, and/or iii) a specific activity of more than 0,053 FVRU/mg protein. Further, the invention relates to use of a xylanase preparation for separating a plant material, such as wheat, into separate useful components as well as processes for such viscosity reduction or separation.

11 Claims, 3 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
  ( A ) LENGTH: 1327 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: CDS
  ( B ) LOCATION: join(4..1221, 1225..1314, 1318..1326)

( x i ) SEQUENCE DESCRIPTION: SEQ ID NO:1:

```
AAA ATG GTC GGA CTG CTT TCA ATC ACC GCG GCG CTT GCC GCG ACT GTG        48
    Met Val Gly Leu Leu Ser Ile Thr Ala Ala Leu Ala Ala Thr Val
    1               5                   10                  15

TTG CCA AAC ATT GTC TCT GCC GTT GGT CTG GAT CAG GCT GCA GTT GCC        96
Leu Pro Asn Ile Val Ser Ala Val Gly Leu Asp Gln Ala Ala Val Ala
                20                  25                  30

AAA GGA CTT CAA TAC TTT GGC ACA GCT ACG GAT AAT CCC GAG CTC ACG       144
Lys Gly Leu Gln Tyr Phe Gly Thr Ala Thr Asp Asn Pro Glu Leu Thr
            35                  40                  45

GAT ATT CCA TAC GTT ACT CAG CTG AAC AAC ACC GCG GAC TTT GGT CAA       192
Asp Ile Pro Tyr Val Thr Gln Leu Asn Asn Thr Ala Asp Phe Gly Gln
        50                  55                  60

ATT ACC CCT GGA AAC TCG ATG AAG TGG GAT GCC ACA GAA CCA TCT CAG       240
Ile Thr Pro Gly Asn Ser Met Lys Trp Asp Ala Thr Glu Pro Ser Gln
    65                  70                  75

GGC ACC TTC ACG TTC ACG AAA GGC GAT GTC ATT GCA GAT CTG GCT GAG       288
Gly Thr Phe Thr Phe Thr Lys Gly Asp Val Ile Ala Asp Leu Ala Glu
80                  85                  90                  95

GGT AAT GGC CAA TAT CTC CGA TGT CAT ACT CTG GTT TGG TAT AAT CAG       336
Gly Asn Gly Gln Tyr Leu Arg Cys His Thr Leu Val Trp Tyr Asn Gln
                100                 105                 110

CTA CCT AGC TGG GTG ACT AGC GGA ACT TGG ACT AAT GCT ACT CTC ACC       384
Leu Pro Ser Trp Val Thr Ser Gly Thr Trp Thr Asn Ala Thr Leu Thr
            115                 120                 125

GCC GCA TTG AAG AAC CAC ATC ACG AAT GTG GTG TCG CAC TAC AAA GGG       432
Ala Ala Leu Lys Asn His Ile Thr Asn Val Val Ser His Tyr Lys Gly
        130                 135                 140

AAA TGT CTT CAT TGG GAC GTG GTC AAT GAG GCG TTG AAT GAC GAC GGA       480
Lys Cys Leu His Trp Asp Val Val Asn Glu Ala Leu Asn Asp Asp Gly
    145                 150                 155

ACC TAC CGC ACC AAC ATC TTC TAC ACC ACC ATC GGC GAA GCC TAC ATC       528
Thr Tyr Arg Thr Asn Ile Phe Tyr Thr Thr Ile Gly Glu Ala Tyr Ile
160                 165                 170                 175

CCC ATT GCC TTT GCC GCA GCG GCT GCA GCC GAC CCG GAC GCG AAG CTG       576
Pro Ile Ala Phe Ala Ala Ala Ala Ala Asp Pro Asp Ala Lys Leu
                180                 185                 190

TTC TAC AAT GAC TAC AAC CTC GAA TAC GGC GGC GCC AAA GCC GCC AGC       624
Phe Tyr Asn Asp Tyr Asn Leu Glu Tyr Gly Gly Ala Lys Ala Ala Ser
```

```
                              195                         200                         205
GCC  CGC  GCC  ATT  GTC  CAG  CTG  GTC  AAG  AAT  GCA  GGT  GCC  AAG  ATC  GAC         672
Ala  Arg  Ala  Ile  Val  Gln  Leu  Val  Lys  Asn  Ala  Gly  Ala  Lys  Ile  Asp
          210                      215                      220

GGG  GTA  GGG  TTG  CAG  GCC  CAT  TTC  AGC  GTC  GGC  ACC  GTG  CCG  AGT  ACG         720
Gly  Val  Gly  Leu  Gln  Ala  His  Phe  Ser  Val  Gly  Thr  Val  Pro  Ser  Thr
     225                           230                      235

AGC  TCG  CTC  GTC  TCG  GTG  CTG  CAA  TCT  TTC  ACT  GCG  CTC  GGG  GTC  GAG         768
Ser  Ser  Leu  Val  Ser  Val  Leu  Gln  Ser  Phe  Thr  Ala  Leu  Gly  Val  Glu
240                      245                      250                           255

GTC  GCC  TAC  ACG  GAG  GCC  GAC  GTG  CGC  ATT  CTC  CTG  CCC  ACC  ACC  GCC         816
Val  Ala  Tyr  Thr  Glu  Ala  Asp  Val  Arg  Ile  Leu  Leu  Pro  Thr  Thr  Ala
                    260                      265                      270

ACT  ACC  CTG  GCC  CAA  CAG  TCG  AGC  GAT  TTC  CAG  GCC  CTG  GTG  CAA  TCC         864
Thr  Thr  Leu  Ala  Gln  Gln  Ser  Ser  Asp  Phe  Gln  Ala  Leu  Val  Gln  Ser
               275                      280                      285

TGT  GTG  CAG  ACA  ACG  GGC  TGC  GTC  GGC  TTC  ACT  ATC  TGG  GAT  TGG  ACA         912
Cys  Val  Gln  Thr  Thr  Gly  Cys  Val  Gly  Phe  Thr  Ile  Trp  Asp  Trp  Thr
          290                      295                      300

GAT  AAG  TAC  AGC  TGG  GTT  CCC  AGC  ACG  TTC  TCG  GGC  TAT  GGG  GCG  GCG         960
Asp  Lys  Tyr  Ser  Trp  Val  Pro  Ser  Thr  Phe  Ser  Gly  Tyr  Gly  Ala  Ala
     305                      310                      315

CTA  CCC  TGG  GAT  GAG  AAC  CTG  GTT  AAG  AAG  CCC  GCG  TAC  AAT  GGC  TTG        1008
Leu  Pro  Trp  Asp  Glu  Asn  Leu  Val  Lys  Lys  Pro  Ala  Tyr  Asn  Gly  Leu
320                      325                      330                           335

TTG  GCC  GGC  ATG  GGG  GTT  ACA  GTT  ACC  ACT  ACG  ACT  ACC  ACC  ACC  ACT        1056
Leu  Ala  Gly  Met  Gly  Val  Thr  Val  Thr  Thr  Thr  Thr  Thr  Thr  Thr  Thr
               340                      345                      350

GCT  ACT  GCC  ACT  GGT  AAG  ACT  ACG  ACT  ACC  ACA  ACG  GGT  GCC  ACG  AGC        1104
Ala  Thr  Ala  Thr  Gly  Lys  Thr  Thr  Thr  Thr  Thr  Thr  Gly  Ala  Thr  Ser
          355                      360                      365

ACG  GGG  ACT  ACG  GCT  GCG  CAT  TGG  GGG  CAG  TGT  GGA  GGG  CTC  AAC  TGG        1152
Thr  Gly  Thr  Thr  Ala  Ala  His  Trp  Gly  Gln  Cys  Gly  Gly  Leu  Asn  Trp
     370                      375                      380

AGT  GGA  CCG  ACG  GCG  TGT  GCC  ACT  GGG  TAC  ACC  TGC  ACT  TAT  GTC  AAT        1200
Ser  Gly  Pro  Thr  Ala  Cys  Ala  Thr  Gly  Tyr  Thr  Cys  Thr  Tyr  Val  Asn
385                      390                      395

GAC  TAT  TAC  TCG  CAG  TGT  CTG  TGA  AGT  ATA  GCC  CAA  CCT  AAA  CCT  GCC        1248
Asp  Tyr  Tyr  Ser  Gln  Cys  Leu       Ser  Ile  Ala  Gln  Pro  Lys  Pro  Ala
400                      405                                410

GGC  GTG  CTT  GCC  ATT  CAG  TCA  GTG  AGA  TTT  ATA  TAT  CAC  AAT  ACT  CAA        1296
Gly  Val  Leu  Ala  Ile  Gln  Ser  Val  Arg  Phe  Ile  Tyr  His  Asn  Thr  Gln
415                      420                      425                           430

AAT  TCA  TTG  CTC  GAC  CTC  TGA  AAA  AAA  AAA  A                                   1327
Asn  Ser  Leu  Leu  Asp  Leu       Lys  Lys  Lys
               435
```

( 2 ) INFORMATION FOR SEQ ID NO:2:

( i ) SEQUENCE CHARACTERISTICS:
        ( A ) LENGTH: 439 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Val  Gly  Leu  Leu  Ser  Ile  Thr  Ala  Ala  Leu  Ala  Ala  Thr  Val  Leu
 1                   5                        10                       15

Pro  Asn  Ile  Val  Ser  Ala  Val  Gly  Leu  Asp  Gln  Ala  Ala  Val  Ala  Lys
               20                       25                       30
```

```
Gly Leu Gln Tyr Phe Gly Thr Ala Thr Asp Asn Pro Glu Leu Thr Asp
         35              40              45
Ile Pro Tyr Val Thr Gln Leu Asn Asn Thr Ala Asp Phe Gly Gln Ile
     50              55              60
Thr Pro Gly Asn Ser Met Lys Trp Asp Ala Thr Glu Pro Ser Gln Gly
 65              70              75              80
Thr Phe Thr Phe Thr Lys Gly Asp Val Ile Ala Asp Leu Ala Glu Gly
             85              90              95
Asn Gly Gln Tyr Leu Arg Cys His Thr Leu Val Trp Tyr Asn Gln Leu
             100             105             110
Pro Ser Trp Val Thr Ser Gly Thr Trp Thr Asn Ala Thr Leu Thr Ala
         115             120             125
Ala Leu Lys Asn His Ile Thr Asn Val Val Ser His Tyr Lys Gly Lys
     130             135             140
Cys Leu His Trp Asp Val Val Asn Glu Ala Leu Asn Asp Asp Gly Thr
145             150             155             160
Tyr Arg Thr Asn Ile Phe Tyr Thr Thr Ile Gly Glu Ala Tyr Ile Pro
             165             170             175
Ile Ala Phe Ala Ala Ala Ala Ala Ala Asp Pro Asp Ala Lys Leu Phe
             180             185             190
Tyr Asn Asp Tyr Asn Leu Glu Tyr Gly Gly Ala Lys Ala Ala Ser Ala
         195             200             205
Arg Ala Ile Val Gln Leu Val Lys Asn Ala Gly Ala Lys Ile Asp Gly
     210             215             220
Val Gly Leu Gln Ala His Phe Ser Val Gly Thr Val Pro Ser Thr Ser
225             230             235             240
Ser Leu Val Ser Val Leu Gln Ser Phe Thr Ala Leu Gly Val Glu Val
             245             250             255
Ala Tyr Thr Glu Ala Asp Val Arg Ile Leu Leu Pro Thr Thr Ala Thr
             260             265             270
Thr Leu Ala Gln Gln Ser Ser Asp Phe Gln Ala Leu Val Gln Ser Cys
         275             280             285
Val Gln Thr Thr Gly Cys Val Gly Phe Thr Ile Trp Asp Trp Thr Asp
     290             295             300
Lys Tyr Ser Trp Val Pro Ser Thr Phe Ser Gly Tyr Gly Ala Ala Leu
305             310             315             320
Pro Trp Asp Glu Asn Leu Val Lys Lys Pro Ala Tyr Asn Gly Leu Leu
             325             330             335
Ala Gly Met Gly Val Thr Val Thr Thr Thr Thr Thr Thr Thr Thr Ala
             340             345             350
Thr Ala Thr Gly Lys Thr Thr Thr Thr Thr Thr Gly Ala Thr Ser Thr
         355             360             365
Gly Thr Thr Ala Ala His Trp Gly Gln Cys Gly Gly Leu Asn Trp Ser
     370             375             380
Gly Pro Thr Ala Cys Ala Thr Gly Tyr Thr Cys Thr Tyr Val Asn Asp
385             390             395             400
Tyr Tyr Ser Gln Cys Leu Ser Ile Ala Gln Pro Lys Pro Ala Gly Val
             405             410             415
Leu Ala Ile Gln Ser Val Arg Phe Ile Tyr His Asn Thr Gln Asn Ser
             420             425             430
Leu Leu Asp Leu Lys Lys Lys
             435
```

PROCESSING PLANT MATERIAL WITH XYLANASE

CROSS-REFERENCE TO RELATED APPLICATIONS

This application is a 35 U.S.C. 371 national application of PCT/DK95/00082 filed Feb. 24, 1995, which is incorporated herein by reference.

FIELD OF THE INVENTION

The present invention relates to the use of a xylanase preparation for reducing the viscosity of a plant material and for separating a plant material, such as wheat, into separate useful components as well as processes for such viscosity reduction or separation.

BACKGROUND OF THE INVENTION

Wheat contains valuable components of gluten and starch which can be recovered in wet milling processes. Vital gluten is the primary product, whereas high quality A-starch and low quality B-starch are valuable by-products. Residual fibre and soluble solids are further by-products.

The commercially available *Trichoderma reesei* cellulase enzyme preparation, Spezyme® CP (Genencor, USA) has been suggested for lowering the viscosity and improving wheat and corn starch processing.

Weegels et al., (1992), describe the use of enzymes (cellulase, hemicellulase, lipase and protease/amylase) in a wheat separation process. It is concluded that cellulases and hemicellulases improve the processing properties of wheat and increase the yield of gluten and starch. The hemicellulase used was a xylanase preparation containing significant side-activities including amylase and protease activity.

It is known that xylanases are capable of degrading wheat flour and other plant derived materials into a number of different degradation products. Xylanases purified from a strain of the fungal species *Aspergillus awamori* have been described in a number of references, c.f., e.g. Kormelink et al., (1993) disclosing physicochemical and kinetic characteristics of three *A. awamori* endo-xylanases. The degradation products obtained by use of such *A. awamori* xylanases in the enzymatic degradation of various plant materials including rice bran, oat spelts, wheat flour, larch wood and birch wood are described by, inter alia, Kormelink et al., (1991), Kormelink et al., (1992), J. M. Kormelink and A. G. J. Voragen (1993), Gruppen et al., (1992), and Gruppen et al., Symposium October 1993.

Voragen et al., (1992), and Gruppen et al., (1993a and 1993b) disclose the degradation of water-extractable and water-unextractable arabinoxylan fractions isolated from wheat flour with *A. awamori* endo-xylanases. The latter reference describes the use of two of the *A. awamori* xylanases in the baking of wheat loaves.

Shei et al., (1985), and Fournier et al., (1985), describe purification and characterization of endoxylanases isolated from A. niger.

None of the above references mentions that xylanases may be used in separation of wheat nor how to select xylanases of particular use for said purpose.

Düsterhöft et al., Symposium October 1993, describe the use of endoxylanase in degradation of non-starch polysaccharides in animal feed and Viëtor et al., (1993), the use of endoxylanase in reducing the viscosity of wort during the beer brewing process.

It is an object of the present invention to provide improved processes for modifying the viscosity of a plant material and for separation of a plant material into desirable components.

BRIEF DISCLOSURE OF THE PRESENT INVENTION

Figure 1:
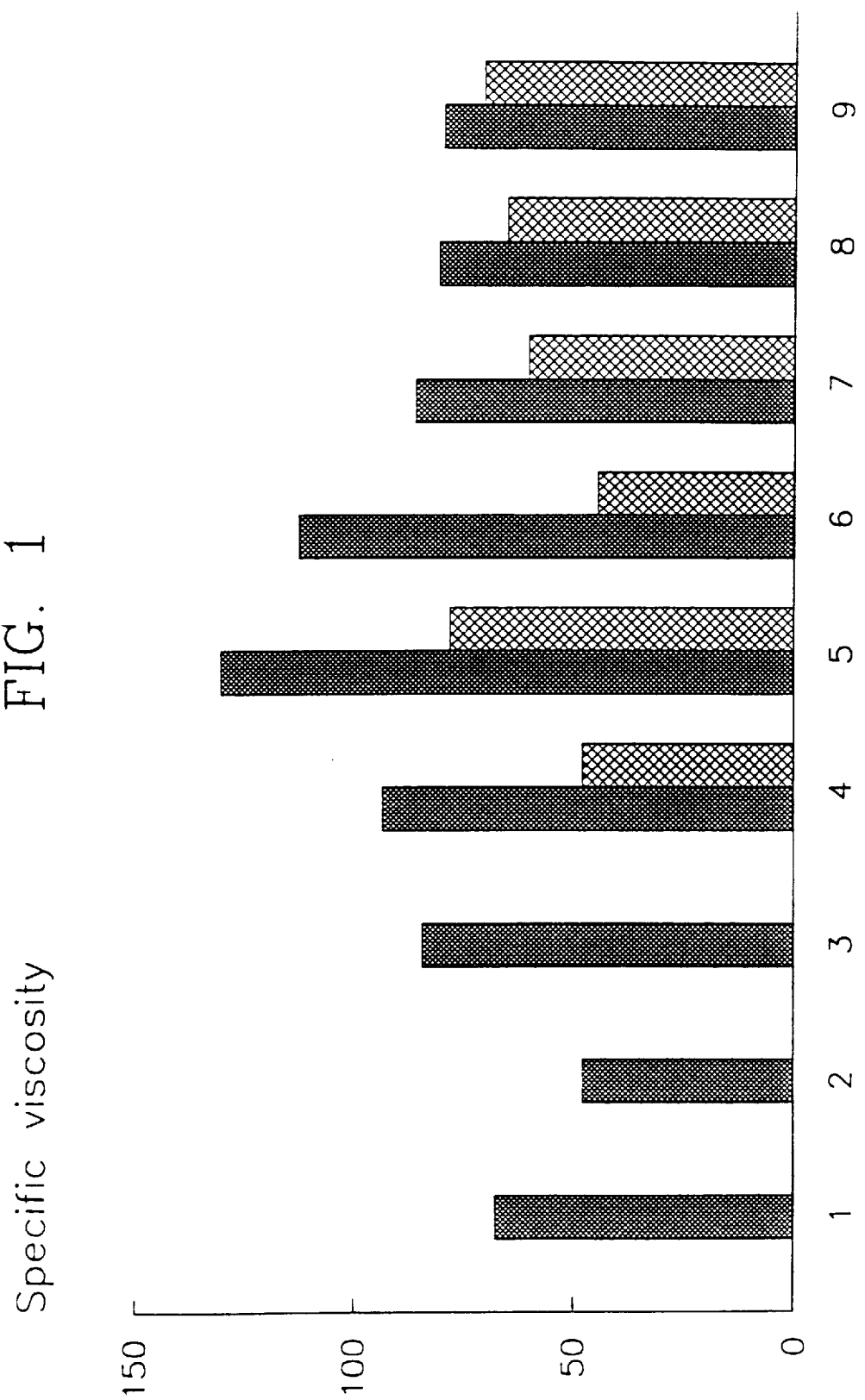
FIG. 1 shows the specific viscosity of xylanase II combined with other enzymes.

The present inventors have now surprisingly found that the activity of xylanase on water soluble and water insoluble pentosans, respectively, seems to be important for the efficiency of the xylanase in reducing the viscosity and/or separation of components of a plant material. The present invention is based on this finding.

Accordingly, in a first aspect the invention relates to the use of a xylanase preparation for modifying the viscosity of a plant material, in which the xylanase preparation exhibits a) a WSPS per mg protein added of at least 0.06, and/or b) a WSPU per mg protein added of at least 15, and/or c) a specific activity of at least 0.053 FVRU/mg protein.

In a second important aspect the invention relates to a xylanase preparation exhibiting the above described characteristics a)–c). Further the invention relates to the use of such preparation for a number of purposes.

In the present context, WSPU (Water Soluble Pentosan Unit) is defined as the activity of the xylanase preparation per mg protein on water soluble pentosans and WIPU (Water Insoluble Units) as the activity on water insoluble pentosans per mg protein where the activities are measured as reducing sugars. The production of soluble and insoluble pentosans, respectively, is described in the Materials and Methods section below. In Example 4 an assay for determining WSPU and WIPU is described. WSPS is the ratio between WSPU and WIPU per mg protein added where the protein is determined according to Kjeldahl, cf the Materials and Methods section herein.

In the present context, the term "protein added" is intended to be the amount of protein comprising xylanolytic activity, which is recovered from a fermentation broth in which the enzyme has been produced, and which subsequently is used for the present purpose. Thus, when assessing the WSPS, WSPU and FVRU values as defined herein of a given enzyme, the term "mg protein" refer to the mg protein associated with the enzyme when recovered from the fermentation broth and not any inert or non-xylanolytic protein added.

It will be understood that xylanase preparations to be used for the present purpose contain a substantial xylanolytic activity per mg protein compared to prior art xylanases and cellulases. This means that by use of a surprisingly low dosage (in mg protein) of the xylanase preparation of the invention, a substantial viscosity reduction (expressed as specific viscosity) and wheat separation capacity, respectively, is obtained. The enzyme to be used in the present invention is preferably substantially a mono-component enzyme which typically may be produced with a high efficiency by use of recombinant DNA techniques in a highly pure form (i.e. comprising relatively low amounts of undesired side-activities (compared to the xylanolytic activity).

FVRU is defined as the specific viscosity of the enzyme relative to the specific viscosity of a standard enzyme preparation of a xylanase produced by *Bacillus pumilus*

DSM 6124 as described in WO 92/03540 per mg protein added. Said enzyme is termed B. pumilus xylanase in the following disclosure. The specific viscosity of the B. pumilus preparation is measured in relation to mg B. pumilus xylanase protein added. The specific viscosity may be determined as described in Example 1.

The above defined class of xylanases are contemplated to be of particular use in wheat separation. Thus, the present inventors have observed that xylanases having a good performance in wheat separation degrade the water soluble wheat pentosans very fast and water insoluble wheat pentosans at a very low rate. Without being limited to any theory it is presently believed that the good performance in wheat separation is caused by a degradation of the viscous water soluble pentosans. The low degradation of insoluble pentosans is also important in the viscosity reduction obtained by xylanases as defined herein since the solubilized insoluble pentosans may increase the viscosity.

In further aspects the invention relates to a process for separating a plant material into components of interest and a process for modifying the viscosity of a plant material, in which processes a xylanase preparation as defined above is used.

DETAILED DISCLOSURE OF THE INVENTION

The xylanase preparation

As will be understood from the above disclosure the activity (as defined in terms of WSPS or WSPU) of the xylanase preparation to be used for the present purpose is believed to be critical. It is preferred that the xylanase preparation to be used for the present purpose is one having a WSPS per mg protein added which is higher than 0.06. Preferably the WSPS added is in the range of 0.06 to at most 10.0 per mg protein, more preferably of at least 0.7 to at most 8.0 per mg protein, still more preferably between 0.9 and 6.0 per mg protein, especially of at least 1.5 to 4.0 per mg protein, and/or a WSPU per mg protein added which is higher than 15, such as 25 or more. Preferably the WSPU per mg protein added is at least 100 to at most 150.000, more preferably at least 130 to at most 120.000, such as at least 160 to at most 100.000, more preferably of at least 300 to at most 90.000, and still more preferably of at least 20.000 to at most 85.000, and/or a specific activity of at least 0.053 FVRU/mg protein. Preferably the specific activity is in the range 0.053 to 3.0 FVRU/mg protein, such as between 0.4, 0.5 or 0.6 and 3.0 FVRU/mg protein, more preferably between 0.1 and 2.0 FVRU/mg protein, still more preferably between 0.4 and 1.0 FVRU/mg protein.

While the xylanase preparation to be used for the present purpose may be of any origin including mammalian, plant or animal origin it is presently preferred that the xylanase is of microbial origin. In particular the xylanase preparation may be one derivable from a filamentous fungus or a yeast.

Xylanases have been found in a number of fungal species, in particular species of Aspergillus, such as A. niger, A. awamori, A. aculeatus and A. oryzae, Trichoderma, such as T. reesei or T. harzianum, Penicillium, such as P. camenbertii, Fusarium, such as F. oxysporum, and Humicola, such as H. lanuginosa, and H. insolens. Xylanases have also been found in bacterial species, e.g. within the genus Bacillus, such as B. pumilus.

A xylanase preparation to be used for the present purpose may be provided by a method which comprises a) isolating a xylanase preparation from any xylanase-producing organism by methods known in the art, and subsequently b) testing the WSPS, WSPU and/or FVRU activity of the xylanase as described herein in order to asses whether it is suitable for the present purpose.

The xylanase-producing organism referred to in a) may be an organism which is a natural producer of xylanase or an organism which has been transformed with DNA encoding the xylanase in question.

It has been found that the fungal species A. aculeatus, in particular the strain CBS 101.43, produces a xylanase of particular use for the present purpose. Said xylanase is termed Xylanase II (or Xyl II) in the present disclosure and is further described in WO 94/21785 hereby included in the present application.

In Example 4 the WSPS and WSPU values, respectively, of a number of prior art xylanases are listed together with that of xylanase II. Furthermore, the effect in wheat separation (expressed as FVRU) of these enzymes is shown. It is apparent that none of these prior art xylanases exhibit a wheat separation effect comparable to that of xylanase II disclosed herein.

The DNA sequence encoding Xylanase II is shown in SEQ ID NO: 1 and the corresponding amino acid sequence in SEQ ID NO: 2. It is contemplated that xylanases exhibiting homology to xylanase II may have a similar activity pattern as xylanase II and thus be useful for the present purpose. Accordingly, in a particularly preferred embodiment the xylanase to be used in the present invention is one, which i) is encoded by the DNA sequence shown in SEQ ID NO: 1 of WO 94/21785 or an analogue thereof encoding a homologue of Xylanase II, ii) comprises the amino acid sequence shown in SEQ ID NO: 2 or a homologous sequence thereof, and/or iii) is immunologically reactive with an antibody raised against a purified xylanase derived from Aspergillus aculeatus, CBS 101.43.

In the present context, the term "homologue" is intended to indicate a polypeptide exhibiting xylanase activity (in terms of WSPS, WSPU and/or FVRU as defined herein) encoded by a DNA sequence hybridizing with an oligonucleotide probe prepared on the basis of the DNA sequence coding Xylanase II enzyme under certain specified conditions (such as presoaking in 5×SSC and prehybridizing for 1 h at ~40° C. in a solution of 5×SSC, 5×Denhardt's solution, 50 mM sodium phosphate, pH 6.8, and 50 μg of denatured sonicated calf thymus DNA, followed by hybridization in the same solution supplemented with 50 μCi 32-P-dCTP labelled probe for 18 h at ~40° C. followed by washing three times in 2×SSC, 0.2% SDS at 40° C. for 30 minutes). More specifically, the term is intended to refer to a DNA sequence which is at least 70% homologous to the DNA sequence shown in SEQ ID NO: 1 or a substantial part thereof, such as at least 75%, at least 80%, at least 85%, at least 90% or even at least 95% homologous to the DNA sequence of SEQ ID NO: 1 or a substantial part thereof encoding a polypeptide with xylanase activity. The term is intended to include modifications of the DNA sequence SEQ ID NO: 1, such as nucleotide substitutions which do not give rise to another amino acid sequence of the xylanase, but which correspond to the codon usage of the host organism into which the DNA construct is introduced or nucleotide substitutions which do give rise to a different amino acid sequence and therefore, possibly, a different protein structure which might give rise to a xylanase mutant with different properties than the native enzyme. Other examples of possible modifications are insertion of one or more codons into the sequence, addition of one or more codons at either end of the sequence, or deletion of one or more codons at either end or within the sequence. It will be understood that the homologue of xylanase II defined herein may comprise a number of different amino acid residues as long as the xylanase activity is as defined herein.

The production of Xylanase II and further characterization thereof is apparent from the disclosure presented in WO 94/21785 included in the present application.

The xylanase preparation to be used herein may be obtained from the microorganism in question by use of any suitable technique. For instance, a xylanase preparation may be obtained by fermentation of a microorganism and subsequent isolation of the enzyme by a method known in the art, but more preferably by use of recombinant DNA techniques known in the art. Such method normally comprises cultivation of a host cell transformed with a recombinant DNA vector capable of expressing and carrying a DNA sequence encoding the xylanase in question, in a culture medium under conditions permitting the expression of the enzyme and recovering the enzyme from the culture.

Within the scope of the invention are any enzyme preparations prepared from microbially derived mono-component enzymes (i.e. substantially without any side activity) having the above defined xylanase features a)–c ). The xylanase of the invention can be identified by determining the WSPS, WSPU and FVRU values, after isolating the component enzymes.

The DNA sequence encoding the xylanase to be used may be of any origin, e.g. a cDNA sequence, a genomic sequence, a synthetic sequence or any combination thereof. The preparation of a xylanase suited for the present purpose is described in detail in WO 94/21785.

When the xylanase is to be used in a process of the invention for separation of wheat (or other processes in which starch is to be produced) it is preferred that the xylanase preparation is substantially free from amylase, in that any amylase activity present may degrade the starch to be produced. Correspondingly, when the xylanase is to be used in the production of proteins, e.g. in a wheat separation process of the invention in which gluten is produced, it is preferred that the xylanase preparation is substantially free from protease, in that the latter enzyme may harm the gluten to be produced. Amylase and protease activities can be removed by methods known in the art. One example is thermo-inactivation which is of particular advantage in connection with xylanase II produced in *Aspergillus oryzae*, in that Xylanase II, in general, is more thermo-stable than amylases and proteases produced by said host cell.

It has been found that the xylanase effect obtained in the plant material separation process of the invention may be considerably improved when the xylanase is used together with a cellulase.

Accordingly, the xylanase preparation to be used in the present invention may comprise a cellulase. The cellulase is preferably of microbial origin, such as derivable from a strain of a filamentous fungus (e.g. Aspergillus, Trichoderma, Humicola, Fusarium). Specific examples of cellulases suitable for the present purpose include the endo-glucanase (endo-glucanase I) obtainable from *H. insolens* and further defined by the amino acid sequence of FIG. 14 in WO 91/17244 and the 43 kD *H. insolens* endoglucanase described in WO 91/17243.

Commercially available cellulase preparations which may be used in combination with a xylanase as described herein include Celluclast® (available from Novo Nordisk A/S), Spezyme® CP (available from Genencor, USA) and Rohament® 7069 W (available from Röhm, Germany).

The plant material separation process

While any plant material comprising xylan (such as softwood and hardwood) may be treated in accordance with the invention it is preferred that the plant material is derived from the family Poaceae (Syn: Graminaceae) and in particular prepared from a cereal such as wheat, rye, barley or oat. The plant material may in addition be of vegetable or fruit origin, e.g. prepared from maize, rice, sorghum bean, or fruit hulls. The plant material may be prepared from any combination of the above mentioned plants and may, in addition comprise non-plant materials.

The plant material to be treated according to the present invention may be in any suitable form. As it will be further explained below, the plant material may conveniently be in the form of a pumpable dispersion or solution allowing a continuous process to be performed. This dispersion is normally made by mixing dry milled material, especially wheat with a mean particle size of 50–100 $\mu$m and water.

The presently preferred plant material to be processed according to the invention is wheat. By the process of the invention the wheat is separated into a gluten, a starch and a fibre fraction. The gluten so produced may, e.g., be added to flour in order to improve the baking properties thereof, or may be used to improve the nutritional value of products such as meat, breakfast cereals and pet food. The starch may, e.g., be used for syrup production, in the paper industry, e.g. for paper coating, and in the textile industry. The fibre fraction may, e.g., be used for animal feed.

Figure 2:
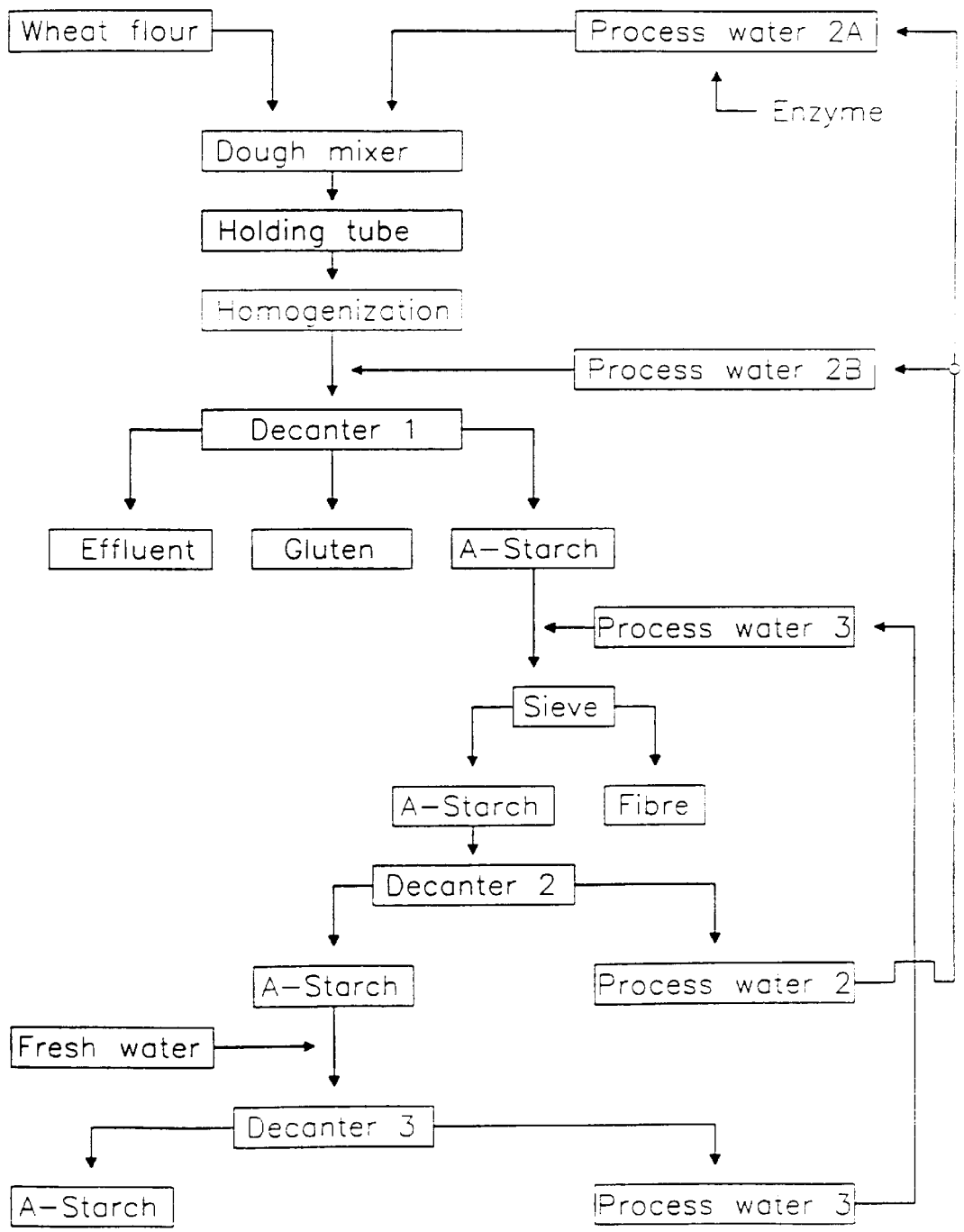
FIG. 2 shows the principle in the wet milling wheat separation process.

In the following the process of the invention for separation of a plant material will be described with reference to wheat separation. However, it will be understood that separation of any of the other types of plant material mentioned above may be performed by a similar type of process and the person skilled in the art would know which type of process to select for separation of a given plant material, cf, for instance, the book entitled "Starch production technology", Ed. by J. A. Radley. In FIG. 2 a flow sheet illustrating a wheat separation process is shown.

The process of the present invention may be carried out by any industrial wheat separation process known in the art. However, it is presently preferred to use a so-called batter process (or wet milling process), in which the starting material is a dilute pumpable dispersion of the wheat to be separated. Normally, the dispersion is made from wheat flour and water. The dry matter content of the dispersion is normally in the range of 35–50%. Two major types of batter processes are known: the hydroclone process and the decanter process. These processes are advantageous in that the water consumption is relatively low.

In the hydrocyclone process the flour is first mixed with water to make a dough, which is then further diluted and passed to an agitated agglomeration tank where gluten is agglomerated. The dispersion with the small gluten agglomerates and starch is pumped to a set of hydrocyclones, where a centrifugal separation takes place. The gluten and the "B"-starch being the lightest fraction leaves the top of the hydrocyclones together and the gluten is separated from the "B"-starch by screens. The underflow from the hydrocyclones consists mainly of "A"-starch, while pentosan (or fibres) are found in both fractions. The fractions are further cleaned by a series of washing/concentration steps.

The decanter process differs from the hydrocyclone process in at least one major point namely when the gluten is agglomerated. In the decanter process it is very important that the concentration of the batter is kept low so as to avoid that the gluten forms bigger lumps before the separation in a two-phases or three-phases decanter. Before the separation the mixed flour/water dispersion is pumped through a homogenizer—a special pin mill with high shear forces starting the agglomeration of the gluten and just before the separation an additional dilution of the dispersion takes place. In case of a two-phases decanter the underflow contains rather clean "A"-starch and the overflow contains gluten, "B"-starch and pentosans. For three-phases decanters the two phases beside the "A"-starch contains gluten with some "B"-starch and a phase with "B"-starch and pentosans.

When a xylanase as defined herein is used for the separation of wheat it is possible to obtain an improved capacity of dough mixing and homogenization, an improved separation capacity, a reduced viscosity in the pentosan fraction (which reduces energy consumption when evaporating and drying) and a reduced ampere consumption on decanters. Furthermore, end products of a higher purity may be obtained and the processing time may be reduced due to the increased flow enabled by the reduced viscosity.

The plant material separation process is normally conducted at a pH in the range of 3–8, such as 4–7 and in particular in the range of 5.5–6.5. Typically, the temperature in the range of 15°–50° C. such as 35°–45° C. In the wheat separation process, the separation according to the invention is normally achieved in 1–5 minutes at a temperature of 40° C.

For some purposes it may be advantageous to use another enzyme together with the xylanase. For instance, it has been found that the combined use of xylanase as defined herein and a cellulase has a synergistic effect. Suitable types of cellulases are mentioned above in the section entitled "The xylanase preparation". The cellulase may be used in an amount corresponding to 0–30,000 EGU per kg of flour, preferably in an amount corresponding to 200–5000 EGU/kg of flour.

Viscosity reduction

As mentioned above the xylanase preparation defined herein may be used for reducing the viscosity of a plant material. The viscosity reduction may be important, e.g. in a continuous wheat separation process as described herein, in that an increased wheat flour flow may be obtained. Furthermore, the viscosity reduction is important in the preparation of food or feed and in brewing, cf Visser et al., Xylans and Xylanases, (1991).

Brewing

The xylanases described herein are contemplated to be of particular use for reducing the viscosity of the wort in the brewing process. The xylanases may be used in connection with wort prepared from barley and sorghum and may be used in the same manner as pentosanases conventionally used for brewing, cf e.g. Viëtor et al., (1993) and EP 227 159.

Feed

The feed to be prepared is normally based on the plant materials identified above, such as cereals, and in particular wheat and/or barley. The xylanase exerts its effect by degrading arabino-xylan contained in the plant material whereby an improved overall utilization of the energy-containing and other nutritional components of the animal feed is obtained. Furthermore, especially as concerns broilers the viscosity of the chyme may be reduced. A reduced viscosity is contemplated to be important for the digestibility of the feed possibly due to a better access of the endogenous enzymes to substrates or to increased diffusibility of digestion products, which results in an increased absorption. In addition, the degradation may help to stabilize the intestinal microbial flora by making the nutrients more readily available. The feed to be prepared may, e.g., be feed for broilers, laying hens and piglets. The xylanase may be incorporated in the feed in any suitable dosage such as 5–2000 FXU/kg of feed, preferably 20–1000 FXU/kg of feed.

Preparation of β-glucan and other cereal components

The xylanase preparation disclosed herein is considered to be of particular use for the preparation of β-glucan by degradation of arabinoxylan present in, e.g., non-starch polysaccharide waste products. The β-glucan may be used as a gum or a bulking agent (in degraded form).

Furthermore, from the above disclosure it is evident that the xylanase preparation may be used in the preparation of starch, in particular wheat starch and gluten.

MATERIALS AND METHODS

Productions of soluble pentosan (WSP) from wheat flour 100 kg common wheat flour was suspended in 300 kg cold water. After stirring for 1 hour the sludge was removed using a decanter. The resulting supernatant was then subjected to enzymatic treatments to remove starch and protein. After adjusting pH to 6.5 and the temperature to 90° C. was first added 2% (of d.m.) of Termamyl® 120L with 90 min. of stirring, followed by a similar treatment with 3% (of d.m.) AMG® 300L at pH 4.6 and 60° C. for 120 min to hydrolyse the starch fraction. Finally, the supernatant was treated with 1% (of d.m.) of Alcalase® 2.4L at pH 8.0 and 55° C. for 120 min under constant stirring. After hydrolysis of starch and protein the product was filtered on filterpress using Seitz-filter K250 to remove residual insoluble material, and the supernatant ultrafiltrated using a 10,000 MW cut-off membrane to remove products from the starch and protein hydrolysis. The retentate was further diafiltrated until 0°BRIX was reached. The product was concentrated by evaporation on a Luwa Evaporater and finally freeze dried.

Production of insoluble pentosan (WIP) from wheat flour 150 kg of common wheat flour was suspended in 450 kg of cold water. The suspension was heated to 60° C. and 600 g of Termamyl® 120L were added. After heating to 95° C. resulting in gelatinization of the starch fraction, the suspension was cooled to 60° C. with continued hydrolysis for 180 min. After adjusting the pH to 8.0 using NaOH 300 g of Alcalase® 2.4L were added. During hydrolysis of protein under constant stirring, the pH was maintained between 7.5 and 8.0 titrating with NaOH. The hydrolysis was continued for 120 min. the precipitate was recovered after centrifugation, washed with water once and then further washed on a 35 μm sieve with cold water to remove all residual soluble material. To the resulting insoluble material up to 20 l of water was added, heated to 60° C. and after an adjustment of the pH to 8.0 with NaOH 100 g of Alcalase® 2.4L were added. The hydrolysis and NaOH-titration were continued until no further drop in pH was observed. The material was then washed again on a 35 μm sieve until all soluble material was removed and, finally, freeze dried.

The activity of the xylanase to be used in the present invention is measured by the release of reducing sugars from soluble pentosan (diluted 25× after incubation), and insoluble pentosan (diluted 5× after incubation).

0.5% of water soluble or water insoluble pentosans produced as described above is dissolved or suspended in a 0.1M citrate/phosphate buffer, pH 6.0. Per sample 0.9 ml of the substrate is mixed with 0.1 ml of enzyme solution. The substrate is held on ice before and during the mixing of enzyme and substrate. Incubation takes place at 40° C. for 15 min. whereafter the enzyme is denatured at 100° C. for 5 min. When the samples are cooled the soluble pentosan solutions are diluted 25 times while the insoluble solutions are diluted 5 times. Then, reducing sugars are determined by reaction, in microtiter plates, with a PHBAH reagent comprising 0.15 g of para hydroxy benzoic acid hydrazide (Sigma H-9882), 0.50 g of potassium-sodium tartrate (Merck 8087) and 2% NaOH solution up to 10.0 ml. Results of blanks are subtracted. Xylose is used as a standard. The reducing sugars may be used in determining WSPU and WSPS.

Protein assay—Kjeldahl

The assay was performed by use of a Tecator Digestor and distillation unit type 1003.

Destruction (Tecator Digestor)

The samples to be analyzed are transferred to Kjeldahl tubes, for fluid samples approx. 1.5 g and for freeze-dried samples approx. 0.1 g. To the samples are added:

a) 3.0 ml sulphuric acid (conc. $H_2SO_4$)
b) 1.5 ml hydrogen peroxide (32% $H_2O_2$)
c) 1 Kjeltab (Se+$K_2SO_4$)

If the samples foam after addition of the chemicals they are not destructed till the next day. Under normal circumstances the samples are placed in the destruction block after 10 min. The block temperature is set to 370° C. When the samples are clear or faintly yellow, they are removed. The destruction usually takes ½–1 hour according to the composition of the sample. The samples are cooled at room temperature for about 20 min. Then they are ready for distillation.

Distillation (Tecator distillation unit type 1003)

The samples are distilled in 25 ml 2% boric acid containing Kjeldahl indicator (A: 0.12 g Methylene blue in 100 ml 96% alcohol and B: 0.125 g Methylene red in 100 ml 96% alcohol, A and B being mixed in the proportion 1A:2B). The destructed sample is mixed with 32.5% NaOH. The ammonium is distilled into the 2% boric acid which is then titrated with 0.1N HCl until pH reaches 4.85.

Determination of endo-glucanase activity (EGU)

Analytical methods

The fermentation broths are analyzed by vibration viscosimetry on CMC at pH 6.0. More specifically, a substrate solution containing 34.0 g/l CMC (Blanose Aqualon) in 0.1M phosphate buffer, pH 6.0 is prepared. The enzyme sample to be analyzed is dissolved in the same buffer. 14 ml substrate solution and 0.5 ml enzyme solution are mixed and transferred to a vibration viscosimeter (e.g. MIVI 3000 available from Sofraser, France) thermostated at 40° C. Endoglucanase unit (EGU) is determined as the ratio between the viscosity of the sample and the viscosity of a standard enzyme solution.

Determination of xylanase activity (FXU)

The endo-xylanase activity is determined by an assay, in which the xylanase sample is incubated with a remazol-xylan substrate (4-O-methyl-D-glucurono-D-xylan dyed with Remazol Brilliant Blue R, Fluka), pH 6.0. The incubation is performed at 50° C. for 30 min. The background of non-degraded dyed substrate is precipitated by ethanol. The remaining blue colour in the supernatant is determined spectrophotometrically at 585 nm and is proportional to the endoxylanase activity.

The endoxylanase activity of the sample is determined relatively to an enzyme standard.

The assay is further described in the publication AF 293.6/1-GB, available upon request from Novo Nordisk A/S, Denmark.

Determination of Endo-Glucanase Units (ECU)

The ECU (endocellulose unit) is determined relatively to an enzyme standard.

Endocellulase decomposes carboxylmethylcellulose, CMC. The resulting reduction in viscosity is determined by a CMC-vibration Viscosimeter (e.g. MIVI 3000 available from Sofraser, France).

The prepared substrate solution contain 35 g/l CMC (Blanose Aqualon) in 0.1M phosphate buffer at pH 7.5. The enzyme sample to be analyzed is determined is dissolved in the same buffer.

0.15 ml standard enzyme solution or the unknown enzyme sample are placed in 10 ml test tubes. 5 ml CMC-substrate solution, preheated to 40° C., is added. The joint solution is mixed thoroughly, incubated for 30 minutes and placed in the viscometer.

The method is further described in AF302/1-GB available from Novo Nordisk upon request.

Flour

The flour used in the following examples had the following components:

TABLE 1

Composition of the flours used.

| Component (in pct) | Fakta flour |
| --- | --- |
| Protein | 10.4 |
| Ash | 0.2 |
| Dry substance | 10.5 |
| Composition of carbohydrates (in PCT): | |
| Glucose | 97.7 |
| Arabinose | 1.1 |
| Xylose | 0.9 |
| Galactose | 0.3 |

Fakta flour: a commercial flour of non-specified type ("Luksus hvedemel", prepared by Dagligvaregruppen, DK-7100 Vejle).

EXAMPLES

Example 1

Viscosity reduction of wheat flour

Different xylanases were tested for their viscosity reducing capability in Fakta Flour as defined above.

The xylanases tested were

Spezyme® CP available from Genencor, USA a *H. insolens* xylanase (produced as described in Example 2 of WO 92/17573

Xylanase I powder (produced using Xylanase I (described in WO 94/21785) as the starting material, by solid liquid separation, concentration and freeze drying following standard methods).

Xylanase II (produced as described in WO 94/21785)

a xylanase produced by *B. pumilus* strain DSM 6124 as described in WO 92/03540 (in the following referred to as *B. pumilus* xylanase).

The viscosity reduction was measured by the following method:

100 g of flour is weighed precisely. To 120 ml deionized water held at 35° C. the enzymes mentioned above were added. The enzymes were dosed as follows:

Spezymes® CP: 8.5 FXU (corresponding to 3.4 mg protein)

Xylanase I powder: 28.3 FXU (corresponding to 0.19 mg enzyme protein and 0.24 mg protein)

Xylanase II: 7.5 FXU (corresponding to 0.19 mg enzyme protein and 0.25 mg protein)

*H. insolens* xylanase: 82.2 FXU (corresponding to 2.2 mg enzyme protein and 22.3 mg protein)

*B. pumilus* xylanase: 21 FXU (corresponding to 0.2 mg protein)

A blank sample is used as control (no enzyme added). The flour and water are stirred by hand for 30 sec and then mixed for precisely 30 sec on a blender (Warring, Commercial laboratory blender, Struers, Adjustments OFF 1–7, rotor in bottom (4 blades)) at 7 (maximum speed). It lasts 30 sec to pour the liquid into the measuring tube at the viscometer (Programmable rheometer, model DV-111, Brookfield, Spindel 25, the measuring tube being thermostated at 38° C.). The viscosity at 40 rpm is measured every 15th sec for 4 minutes. The specific viscosity expressed as mean viscosity of sample/mean viscosity of blank in percents is used as a measure of the viscosity reduction. The mean viscosity is a mean of the level reached after 60 sec and until the end of measurements.

The lowest specific viscosity was found in using xylanase II. Other xylanases were found to lower the specific viscosity (Xylanase I, Spezyme® CP) although to a lesser extent. The *H. insolens* xylanase was found to increase the viscosity at this dosage. As an example the above mentioned dosages resulted in specific viscosity of 69% for xylanase II, 78% for xylanase I, 87% for Spezyme® CP and 128% for *H. insolens* xylanase (corresponding to 0.63 FVRU/mg protein, 0.044 FVRU/mg protein, 0.053 FVRU/mg protein and 0.012 FVRU/mg protein).

Example 2

Wheat separation

The wheat separation capacity of the enzymes mentioned in Example 1 were evaluated by a centrifugation test. The test was conducted on the flour mentioned in Example 1.

The flour and water were mixed according to the procedure described in Example 1. After blending 10 ml of the batter was centrifugated (Megafuge 1.0 Heraeus Sepatech) at 4332 g for 5 minutes. The starch was found in the bottom layer, followed by gluten, sludge and the effluent layer at the top. The separation is expressed as an effluent percent. The higher percentage the better separation.

It was confirmed that xylanase II performs best. As an example the effluent of the flour was 14% for a blank sample, 21% for Spezyme® CP, 22% for xylanase I and 23% for xylanase II.

Example 3

Viscosity reduction by Xylanase II combined with another enzyme Different xylanases were tested for their viscosity reducing capability when combined with Xylanase II. The Fakta flour described above was used.

The xylanases tested were

Celluclast® CCN3035 available from Novo Nordisk A/S

Endoglucanase I, a *H. insolens* cellulase comprising the amino acid sequence shown in FIG. 14 in WO 91/17244 and produced as described in said reference 43 kD endo-glucanase, a *H. insolens* cellulase described and produced as described in WO 91/17243 a *H. insolens* xylanase (produced as described in Example 2 of WO 92/17573)

Xylanase I powder (identified above)

*B. pumilus* xylanase (identified above).

Each of the enzymes was used combined with Xylanase II and compared to Spezyme® CP. The viscosity reduction was measured as described in Example 1.

The enzyme dosages were as follows:

Celluclast®: 16 EGU (corresponding to 0.024 ml)

Endoglucanase I: 26.5 ECU (corresponding to 0.0053 ml)

43 kD endo-glucanase: 101 ECU (corresponding to 0.017 ml)

*H. insolens* xylanase: 82.2 FXU (corresponding to 2.2 mg enzyme protein and 22.3 mg protein)

Xylanase I powder: 28.3 FXU (corresponding to 0.19 mg enzyme protein and 0.24 mg protein)

*B. pumilus* xylanase: 21 FXU (corresponding to 0.024 ml and 0.2 mg protein)

Xylanase II: 7.5 FXU (corresponding to 0.19 mg enzyme protein and 0.25 mg protein)

Spezyme® CP: 8.5 FXU (corresponding to 0.024 ml and 3.4 mg protein)

From FIG. 1 it is evident that no other enzymes reduces the viscosity at the same level as Xylanase II does. Furthermore a remarkable reduction of the viscosity is seen when Xylanase II is combined with especially Endoglucanase I and the 43 kD cellulase. Xylanase II can also be combined with existing multi-component enzymes as can be seen with Celluclast®. In FIG. 1 the dark columns indicate the enzyme performance alone. The light columns indicate the observed effect of the enzymes combination with Xylanase II:

| | |
|---|---|
| 1 = Xylanase II | 2 = Xylanase II, |
| 3 = Specyme ®CP | 4 = 43 kD Endoglucanase, |
| 5 = *H. insolens* xylanase | 6 = Endoglucanase I |
| 7 = Xylanase I powder | 8 = Celluclast ® |
| 9 = *B. pumilus* xylanase | |

Example 4

WSPS and WSPU determinations

In determining the WSPS and WSPU the protein content of the added determined according to Kjeldahl and the activities of the enzymes upon water insoluble (WIP) and soluble pentosans (WSP) produced as described previously measured as reducing sugars must be determined.

The WSPS and WSPU values determined for a number of preperations were as follows:

| Enzyme | mg protein pr. kg flour | activity on WSP in µmol/min/ g product | WSPU | activity on WIP in µmol/min/ g product | WSPS |
|---|---|---|---|---|---|
| Xylanase II | 2.5 | 121000 | 48237 | 14600 | 3.3 |
| Spezyme ® CP | 34 | 446 | 13 | 231 | 0.06 |
| *H. insolens* xylanase | 223 | 3406 | 15 | 930 | 0.02 |
| Xylanase I (powder) | 2.4 | 188200 | 79000 | 038100 | 2.1 |

The WSPU is the activity on WSP per mg protein pr. kg flour and the WSPS is the ratio WSP/WIP per mg protein pr. kg flour.

As can be seen Xylanase II exhibits a remarkable high WSPU and WSPS which reflexes the degradation of water soluble pentosans at a high rate and a low degradation at insoluble pentosans compared to protein addition.

Example 5

Use of xylanase in animal feed

Broiler chickens were fed for 6 weeks on an experimental diet with and without enzymes. The diet contained 81% wheat in the first 3 weeks of the trial and 84.5% wheat the last 3 weeks. They were divided into 3 treatments; for the first six weeks each treatment included 12 repetitions with 8 broilers in each, the last 3 weeks 6 repetitions with 5 chickens in each. The treatments included a control without enzymes and the following enzymatic treatments: 400 FXU/ kg feed Bio-Feed™ Plus (BF+) (available from Novo Nordisk A/S) and 400 FXU/kg feed Xylanase II. Both enzymes were formulated as CT granulate according to the method described in WO 92/12645. Weight gain and feed consumption was determined and feed conversion ration (FCR) was calculated from 0 to 3 and from 3 to 6 weeks. Furthermore, jejunal and ileal viscosity was determined on a supernatant from the gut contents, using a Brookfield LVTDV-II viscosimeter.

The results are apparent from the following tables.

TABLE 2

Production parameters from 0 to 3 weeks.

|  | Weight gain/ chick (g) | Feed intake/ chick (g) | Feed conversion (g/g) % |
|---|---|---|---|
| Control | 364.55 | 647.04 | 1.78 100 |
| BF + 400 | 391.88 | 643.68 | 1.64 92 |
| Xyl II 400 | 404.83 | 650.89 | 1.61 90 |

TABLE 3

Production parameters from 3 to 6 weeks.

|  | Weight gain/ chick (g) | Feed intake/ chick (g) | Feed conversion (g/g) % |
|---|---|---|---|
| Control | 835.51 | 1882.44 | 2.22 100 |
| BF + 400 | 932.24 | 1906.70 | 2.06 93 |
| Xyl II 400 | 1050.08 | 2068.44 | 1.98 89 |

TABLE 4

Jejunal viscosity at 3 and 6 weeks.

|  | 3 weeks | 6 weeks |
|---|---|---|
| Control | 16.51 | 6.31 |
| BF + 400 | 11.24 | 12.96 |
| Xyl II 400 | 6.35 | 3.50 |

TABLE 5

Ileal viscosity at 3 and 6 weeks.

|  | 3 weeks | 6 weeks |
|---|---|---|
| Control | 40.07 | 20.41 |
| BF + 400 | 18.46 | 16.92 |
| Xyl II 400 | 15.65 | 6.27 |

As can be seen from table 1 and 2, the FCR is lower in the groups receiving enzymes, both after 3 and 6 weeks. In both cases Xylanase II is better than BF+. This is mainly due to a better growth of the animals in this group.

With regard to jejunal viscosity Xylanase II gives a lower viscosity compared to both BF+ and control. This is also the case for ileal viscosity. Both the control and xylanase II gives a lower viscosity after 6 weeks than 3 weeks, while this is not the case for BF+. It thus seems that xylanase II works better during the last 3 weeks than BF+, which is also indicated by the relatively lower FCR of Xylanase II compared to BF+ at 6 weeks.

This experiment thus shows that Xylanase II gives a better feed conversion than BF+ on the same FXU basis, i.e. that more nutrients are made available with Xylanase II. This may partly be due to a lower ileal viscosity in the xylanase II group.

Example 6

Metabolizable energy of Xylanase II in animal feed

The impact of Xylanase II (100 FXU/kg and 200 FXU/kg) on the AME (Apparent Metabolizable Energy) of wheat was determined by the European reference method (Bourdillon et al., (1990), and compared to the commercial product Bio-Feed™ Plus (400 FXU/kg) (BF+) from Novo Nordisk A/S. The AMEn-value expresses the metabolizable energy in the feed corrected for N-retention.

Day-old male Ross broiler chickens, delivered from a commercial hatchery were used.

From day 1 to day 16 the chickens were fed a commercial starter diet. On day 16 the chickens were weighed individually. Chickens with to high or to low body weight were discarded and the rest were assigned to battery cages. From day 16 to day 23 they were adapted to the cages. The balance trail was carried out in vivo from day 24 to day 28 according to Bourdillon et al., (1990), supra. The trail included 9 treatments with 5 replicates of 4 broiler chickens per replica.

The basal diet contained 56% sorghum, 32.5% soybean meal, 6% animal fat, 1% soybean oil and 5% minerals, vitamins, trace elements and amino acids. In the experimental diet half of the basal diet was replaced by wheat. The chickens were fed diets as mash at a level of 90% of ad libitum intake.

Determination of AMEn

The chicken excreta were collected quantitatively daily. Samples of feed and freeze dried excreta were analyzed for fat, gross energy (GE) and nitrogen.

The AME content of the diets were calculated from their respective excreta/feed ratio as well as their corresponding gross energy (GE) content. Correction for N-retention to zero (AMEn) was done by using an energy equivalent of 34.36 kJ/gN retained.

Fat digestibility was determined by fat extraction of diets and freeze dried excreta.

Figure 3:
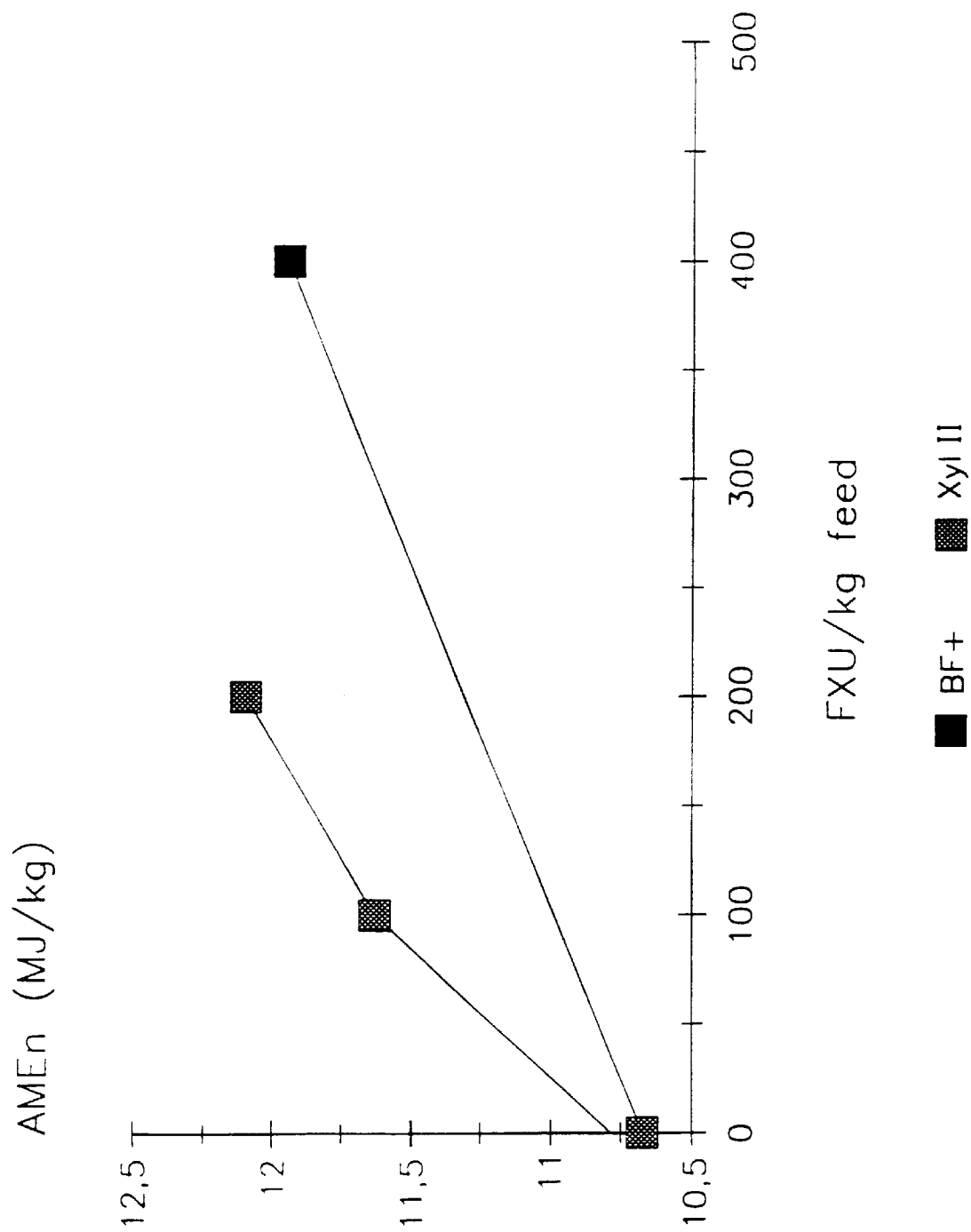
FIG. 3 shows the AMEn of wheat in Broilers. BF+=Bio-Feed® Plus Xyl II=Xylanase II

The determined AMEn is displayed in FIG. 3.

From FIG. 3 it can be seen that the supplementation of the basal diet with Xylanase II resulted in a significant improvement of the metabolizable energy in comparison to Bio-Feed™ (BF+).

REFERENCES

Weegels et al., Starch/Stärke, 44 No. 2, pp. 44–48, 1992.

H. Gruppen et al., Journal of Cereal Science, Vol. 18, pp. 111–128, 1993a.

Kormelink, F. J. M. and Voragen, A. G. J., Appl.Microbiol. Biotechnol., 38, pp. 688–695, 1993.

Kormelink, F. J. M. et al. Journal of Biotechnology., 27, pp. 249–265, 1993.

Kormelink et al., Xylans and Xylanases, Elsevier Science Publishers, 1993, pp. 141–147.

H. Gruppen et al., Carbohydr. Res. 233 (1992), 45–64.

H. Gruppen et al., Journal of Cereal Science, Vol. 18, pp. 129–143, 1993b.

Düsterhöft et al., Symposium: Enzymes in Animal Nutrition, 13–15 Oct., 1993, Kantause Ittingen.

H. Gruppen et al., Symposium: Enzymes in Animal Nutrition, 13–15 Oct., 1993, Kantause Ittingen.

A. G. J. Voragen et al., in "Xylans and Xylanases", Elsevier Science Publishers B. V., 1992, 51–68.

F. J. M. Kormelink and A. G. J. Voragen, in "Xylans and Xylanases", Elsevier Science Publishers, 1993, p. 415–418.

Viëtor et al., 1993, J. Inst. Brew., May–June, 99, pp. 243–248.

Shei, J. C., et al., Biotech. and Bioeng. Vol. XXVII, pp. 533–538, 1985.

Fournier, R. et al., Biotech. and Bioeng. Vol. XXVII, pp. 539–546, 1985.

Bourdillon et al. (1990), Br. Poultry Sci., 31, 557–565)

We claim:

1. An enzyme preparation comprising a xylanase encoded by the nucleic acid sequence of SEQ ID NO: 1, or by a nucleic acid sequence which hybridizes to the DNA sequence of SEQ ID NO: 1 under the following conditions: presoaking in 5×SSC and prehybridizing for 1 hour at about 40° C. in a solution of 5×SSC, 5×Denhardt's solution, 50 mM sodium phosphate, pH 6.8, and 50 μg denatured sonicated calf thymus DNA, hybridization in the same solution for 18 h at about 40° C., followed by washing three times in 2×SSC, 0.2% SDS at 40° C. for 30 minutes.

2. The enzyme preparation of claim 1, wherein the xylanase has the amino acid sequence of SEQ ID NO:2.

3. The enzyme preparation of claim 1, wherein the xylanase is encoded by a DNA sequence isolated from a DNA library of *Aspergillus aculeatus*, CBS 101.43.

4. The enzyme preparation of claim 1, wherein the xylanase exhibits one or more of the characteristics of:
   (a) a ratio of water soluble pentosan unit (WSPU) to water insoluble pentosan unit (WIPU) per mg protein added greater than 0.06;
   (b) a WSPU per mg protein added greater than 15; and
   (c) a specific activity of more than 0.053 specific viscosity (FVRU) per mg protein.

5. The enzyme preparation of claim 1, further comprising a cellulase having a specific activity of at least 10,000 endogluconase units (EGU).

6. A process for reducing the viscosity of a plant material, comprising treating plant material with the enzyme preparation of claim 1.

7. The process of claim 6, wherein the enzyme treatment is performed at a pH in the range of 3–8.

8. The process of claim 6, wherein the enzyme treatment is performed at a temperature in the range of 15°–50° C.

9. The process of claim 6, in which the plant material is a cereal.

10. The process of claim 9, wherein the cereal is one wheat, barley, rye, oat, rice, or sorghum.

11. A method of preparing an animal feed, comprising treating plant material with the enzyme preparation of claim 1.

* * * * *